United States Patent
Paulucci et al.

(10) Patent No.: US 11,980,678 B2
(45) Date of Patent: May 14, 2024

(54) HYBRID MINERAL AND ORGANIC DAILY SUNSCREEN THICK CREAM MOISTURIZER

(71) Applicant: L'OREAL, Paris (FR)

(72) Inventors: Jennifer Lynn Paulucci, Manalapan, NJ (US); Maximillian Baria, River Edge, NJ (US); Jaimie Mecca, Long Hill Township, NJ (US); Patricia Brieva, Manalapan, NJ (US); Rose Maxwell, Brooklyn, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/876,837

(22) Filed: Jul. 29, 2022

(65) Prior Publication Data
US 2024/0033196 A1     Feb. 1, 2024

(51) Int. Cl.
| | |
|---|---|
| *A61K 8/27* | (2006.01) |
| *A61K 8/06* | (2006.01) |
| *A61K 8/37* | (2006.01) |
| *A61K 8/40* | (2006.01) |
| *A61K 8/73* | (2006.01) |
| *A61K 8/891* | (2006.01) |
| *A61Q 17/04* | (2006.01) |

(52) U.S. Cl.
CPC ............... *A61K 8/27* (2013.01); *A61K 8/062* (2013.01); *A61K 8/37* (2013.01); *A61K 8/40* (2013.01); *A61K 8/732* (2013.01); *A61K 8/891* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 2007/0031348 A1* | 2/2007 | Staeb | A61P 17/06 424/47 |
| 2013/0156711 A1 | 6/2013 | Castro | |
| 2014/0161848 A1 | 6/2014 | Ikebe et al. | |
| 2021/0093547 A1 | 4/2021 | Steeley et al. | |
| 2022/0000727 A1 | 1/2022 | Paulucci et al. | |

FOREIGN PATENT DOCUMENTS

| | | |
|---|---|---|
| KR | 102272543 B1 | 7/2021 |
| KR | 20210148578 A | 12/2021 |
| WO | 2017116589 A1 | 7/2017 |
| WO | 2022006408 A1 | 1/2022 |

OTHER PUBLICATIONS

Anonymous, Mintel "AM Facial Moisturizing Lotion with Sunscreen SPF 30", May 2021, Record ID 8715027.
Anonymous, Mintel, "Sun Block UV Shield SPF 50+ PA+++," XP 093046953, Record ID 4287191, Sep. 22, 2016, www.gnpd.com.
Anonymous, Mintel, "Lightweight Sunscreen SPF 50+ PA++++," XP093046897, Record ID 9259844, Dec. 21, 2021, www.gnpd.com.
Anonymous, Mintel, "Qirun Sunscreen Spray SPF 50+ PA+++," XP093046667, Record ID 9491162, Apr. 1, 2022, www.gnpd.com.
Anonymous, Mintel, "Triple Protection Sunscreen Lotion for Babies," XP093047024, Record ID 10139730, Jun. 11, 2023, www.gnpd.com.
Search Report issued to French counterpart Application No. FR2210403 dated May 15, 2023.

* cited by examiner

*Primary Examiner* — Nannette Holloman
(74) *Attorney, Agent, or Firm* — McNees Wallace & Nurick LLC

(57) ABSTRACT

An organic-mineral hybrid sunscreen composition is an oil-in-water emulsion of aqueous and oil phases. The oil phase includes at least one mineral UV filter comprising Zinc oxide, a blend of organic UV filters comprising ethylhexyl methoxycinnamate, ethylhexyl salicylate, octocrylene, and homosalate, at least one oil phase solvent, and at least one surfactant and the water phase includes water; at least one water-miscible solvent, and at least one polymer, and at least one filler. The organic-mineral hybrid sunscreen composition has an SPF of at least about 30 and a critical wavelength of at least 370 nm.

20 Claims, No Drawings

HYBRID MINERAL AND ORGANIC DAILY SUNSCREEN THICK CREAM MOISTURIZER

FIELD OF THE DISCLOSURE

The instant disclosure is directed to organic-mineral hybrid sunscreen compositions, and to methods for using the organic-mineral hybrid sunscreen compositions to protect keratinous substrates such as skin and hair from UV radiation.

BACKGROUND

The negative effects of exposure to ultraviolet ("UV") light are well known. Prolonged exposure to sunlight causes damage such as sunburn to the skin and dries out hair making it brittle. When skin is exposed to UV light having a wavelength of from about 290 nm to about 400 nm, long term damage can lead to serious conditions such as skin cancer.

UV light also contributes to aging by causing free radicals to form in the skin. Free radicals include, for example, singlet oxygen, hydroxyl radical, the superoxide anion, nitric oxide, and hydrogen radicals. Free radicals attack DNA, membrane lipids and proteins, generating carbon radicals. These in turn react with oxygen to produce a peroxyl radical that can attack adjacent fatty acids to generate new carbon radicals. This cascade leads to a chain reaction producing lipid peroxidation products. Damage to the cell membrane results in loss of cell permeability, increased intercellular ionic concentration, and decreased ability to excrete or detoxify waste products. The end result is a loss of skin elasticity and the appearance of wrinkles. This process is commonly referred to as photo-aging.

Sunscreens can be used to protect against UV damage and delay the signs of photo-aging. The degree of UV protection afforded by a organic-mineral hybrid sunscreen composition is directly related to the amount and type of UV filters contained therein. The higher the amount of UV filters, the greater the degree of UV protection. Consumers prefer organic-mineral hybrid sunscreen compositions to include natural and not irritating components that appear natural (unnoticeable) once applied. It is known in the art to that there are challenges to providing mineral and organic UV sunscreen products having a high Sun Protection Factor (SPF) that are shelf stable, capable of maintaining SPF benefit and have desirable aesthetics upon application by the user.

The inventors of the instant disclosure have formulated a hybrid mineral and organic daily sunscreen thick cream moisturizer which exhibits high SPF and critical wavelength, and high emulsion structural stability in the presence of high amounts of mineral-based and organic UV filtering agents that also confers good aesthetics.

SUMMARY OF THE INVENTION

The instant disclosure provides a hybrid organic-mineral hybrid sunscreen composition that includes mineral-based and organic UV filtering agents, which are considered to be non-irritating, natural, and gentle to the skin, together with oil-based solvent, surfactant, thickeners, and ceramides and other skin actives, that confers stable sun protection, pleasing consumer sensorial and textural properties, and emulsion structural stability in the presence of high amounts of mineral UV filters. The hybrid organic-mineral hybrid sunscreen composition overcomes challenges known in the art wherein high levels of mineral UV filters have been shown to be unstable. The hybrid organic-mineral hybrid sunscreen composition has an in vivo SPF 30 and CWL minimum of 370 nm. The UV filters are present with a UVA:SPF having a minimum 1:3 ratio. The hybrid organic-mineral hybrid sunscreen composition has optimized sensorial properties that are pleasing to consumers, and increased stability of the emulsion as compared to a benchmark comparative composition as evidenced 12-week tests and one week 60° C. stability tests.

In a representative embodiment, the organic-mineral hybrid sunscreen composition comprises: an oil-in-water emulsion of aqueous and oil phases, comprising:
a. an oil phase comprising: at least one mineral UV filter comprising Zinc oxide; a blend of organic UV filters comprising ethylhexyl methoxycinnamate, ethylhexyl salicylate, octocrylene, and homosalate; at least one oil phase solvent, and at least one surfactant;
b. a water phase comprising: water; at least one water-miscible solvent; and at least one polymer; and
c. at least one filler,
wherein the organic-mineral hybrid sunscreen composition has an SPF of at least about 30 and a critical wavelength of at least 370 nm, and wherein the composition is free from UV filters selected from menthyl anthranilate (meradimate), parabens or a combination thereof.

In some embodiments, the at least one mineral UV filter comprises Zinc oxide present in an amount that is at least about 8%; the blend of organic UV filters comprises ethylhexyl methoxycinnamate present at about 5%, ethylhexyl salicylate present at about 5%, octocrylene present at about 2%, and homosalate present at about 10%, all amounts by weight, based on the weight of the composition.

In some embodiments, the organic-mineral hybrid sunscreen composition optionally comprises at least one skin active.

In some embodiments, the at least one oil phase solvent comprises dimethicone.

In some embodiments, the at least one surfactant is selected from the group consisting of cationic surfactants comprising a quaternary ammonium salt and a fatty alcohol.

In some embodiments, the at least one water-miscible solvent is selected from the group consisting of mono alcohols, diols, polyols, and combinations thereof.

In some embodiments, the at least one polymer is selected from the group consisting of celluloses, gums, hydrophilic colloids, and combinations thereof.

In some embodiments, the at least one filler is selected from starches.

In some particular embodiments, the organic-mineral hybrid sunscreen composition comprises: an oil-in-water emulsion of aqueous and oil phases, comprising:
a. an oil phase comprising: at least one mineral UV filter comprising Zinc oxide present in an amount that is at least about 8%; a blend of organic UV filters comprising ethylhexyl methoxycinnamate, present at about 5%, ethylhexyl salicylate present at about 5%, octocrylene present at about 2%, and homosalate present at about 10%, all amounts by weight, based on the weight of the composition; at least one oil phase solvent comprising dimethicone, and at least one surfactant comprising cetearyl alcohol (and) behentrimonium methosulfate;
b. a water phase comprising: water; water-miscible solvent comprising glycerin and propanediol; and at least one polymer comprising hydroxyethylcellulose; and c. at least one filler comprising aluminum starch octenylsuccinate, wherein the organic-mineral hybrid sunscreen composition has an SPF of at least about 30 and a critical wavelength of at least 370 nm.

In some particular embodiments, the organic-mineral hybrid sunscreen composition comprises: an oil-in-water emulsion of aqueous and oil phases, comprising:

a. an oil phase comprising: at least one mineral UV filter comprising Zinc oxide present in an amount that is at least about 8%; a blend of organic UV filters comprising ethylhexyl methoxycinnamate, present at about 5%, ethylhexyl salicylate present at about 5%, octocrylene present at about 2%, and homosalate present at 1 about 0%, all amounts by weight, based on the weight of the composition; at least one oil phase solvent comprising dimethicone, present in an amount that is equal to or less than about 2%, and at least one surfactant comprising cetearyl alcohol (and) behentrimonium methosulfate present at about 4.5%;

b. a water phase comprising: water; water-miscible solvent comprising glycerin present at 3% and propanediol present at about 3%; and at least one polymer comprising hydroxyethylcellulose present at about 0.5%; and c. at least one filler comprising aluminum starch octenylsuccinate present at about 0.5%, wherein the organic-mineral hybrid sunscreen composition has an SPF of at least about 30 and a critical wavelength of at least 370 nm.

In some embodiments, the weight ratio of the UV filters to the total amount of the oil phase is about 80% (based on the total weight of the UV filters and the total weight of the oil phase). In some embodiments, the weight ratio of the oil phase solvent to the total amount of the oil phase is equal to or less than about 5% (based on the total weight of the oil phase solvent and the total weight of the oil phase).

In some embodiments, the organic-mineral hybrid sunscreen composition further comprises one or a combination of additives selected from the group consisting of solvents, SPF boosters, humectants, waxes, skin care actives, preservatives, pH adjusters, chelating agents, cooling agents, fragrances, dyes, pigments, and combinations thereof.

In the various embodiments, the organic-mineral hybrid sunscreen composition demonstrates emulsion structural stability wherein the sunscreen composition does not exhibit signs of phase separation, and/or become inhomogeneous after up to 12 weeks in an ambient temperature in the range from about 5° C. up to and including about 45° C., and maintains emulsion structural stability, with minimal color change at 60° C. for at least one week. In the various embodiments, the organic-mineral hybrid sunscreen composition demonstrates an SPF of about 30 and CWL of at least 370 nm.

In some particular embodiments, the organic-mineral hybrid sunscreen composition comprises: an oil-in-water emulsion of aqueous and oil phases, comprising:

a. an oil phase comprising: at least one mineral UV filter comprising Zinc oxide present in an amount that is at least about 8%; a blend of organic UV filters comprising ethylhexyl methoxycinnamate, present at about 5%, ethylhexyl salicylate present at about 5%, octocrylene present at about 2%, and homosalate present at about 10%, all amounts by weight, based on the weight of the composition; at least one oil phase solvent comprising dimethicone, present in an amount that is equal to or less than about 2%, and at least one surfactant comprising cetearyl alcohol (and) behentrimonium methosulfate present at about 4.5%;

b. a water phase comprising: water; water-miscible solvent comprising glycerin present at about 3% and propanediol present at about 3%; and at least one polymer comprising hydroxyethylcellulose present at about 0.5%;

c. at least one filler comprising aluminum starch octenylsuccinate present at about 0.5%; and d. one or a combination of additives selected from the group consisting of solvents, SPF boosters, humectants, waxes, skin care actives, preservatives, pH adjusters, chelating agents, cooling agents, fragrances, dyes, pigments, and combinations thereof, wherein the organic-mineral hybrid sunscreen composition has an SPF of at least about 30 and a critical wavelength of at least 370 nm, and wherein the organic-mineral hybrid sunscreen composition does not exhibit signs of phase separation, and/or become inhomogeneous after up to 12 weeks in an ambient temperature in the range from about 5° C. up to and including about 45° C., and maintains emulsion structural stability, with minimal color change at 60° C. for at least one week.

In various embodiments, the organic-mineral hybrid sunscreen composition may exclude one or more ingredients selected from the group consisting of menthyl anthranilate, parabens, and combinations thereof.

The instant disclosure also relates to methods for protecting skin from UV radiation comprising applying an effective amount of the organic-mineral hybrid sunscreen composition to the skin.

DETAILED DESCRIPTION OF THE DISCLOSURE

Where the following terms are used in this specification, they are used as defined below.

The term "active material" as used herein with respect to the percent amount of an ingredient or raw material, refers to 100% activity of the ingredient or raw material, unless otherwise specified.

The terms "aqueous phase" and "water phase" mean water, water soluble, water miscible and water dispersible ingredients, and represents the sum total of all ingredients in the organic-mineral hybrid sunscreen composition which are water-soluble or water-dispersible, and which are combined together with water during the preparation of the example emulsion compositions.

The term "oil phase" means oil, oil soluble, of miscible and oil dispersible ingredients, and represents the sum total of all ingredients in the organic-mineral hybrid sunscreen composition which are oil-soluble or oil-dispersible, and which are combined together with oil during the preparation of the example emulsion compositions.

The term "critical wavelength" ($\lambda_c$) refers to the wavelength at which the sunscreen allows 10% of the rays to penetrate. A sunscreen with a critical wavelength over 370 nm is considered by the FDA to provide excellent UVA protection.

"Cosmetically acceptable" means that the item in question is compatible with a keratinous substrate such as skin and hair. For example, a "cosmetically acceptable carrier" means a carrier that is compatible with a keratinous substrate such as skin and hair.

The term "homogenous" means in reference to the organic-mineral hybrid sunscreen composition as having the visual appearance of being substantially uniform throughout, i.e., visually lacks separation and pooling of fluid.

The term "keratinous tissue" includes, but is not limited to, skin, hair, and nails.

The term "mineral UV filtering agent" is interchangeable with the terms "mineral UV screening agent," "inorganic UV filtering agent," "inorganic UV screening agent," "mineral UV filter, and "inorganic UV filter." Mineral UV filtering agents are compounds that do not include any carbon atoms in their chemical structures that are capable of screening out, scattering, or absorbing UV radiation between 280 and 400 nm.

The term "SPF booster" refers to a material which increases the UV absorption of another material when the two are intermixed in a composition by refracting UV radiation, thereby increasing the effective path length of the UV radiation through the organic-mineral hybrid sunscreen composition.

The term "emulsion structural stability" refers to the oil-in-water emulsion structural stability and means that the organic-mineral hybrid sunscreen composition exhibits an initially good aesthetic appearance, including lack of a grainy texture, lack of crystal formation, maintains consistent microscopic structure, and does not demonstrate visually perceptible separation of phases, appreciable pooling of fluid, or droplet formation. In addition, the organic-mineral hybrid sunscreen composition retains emulsion structural stability as described above, and maintains consistent color, odor, and viscosity during extended storage including storage up to 12 weeks, in particular after exposure to an ambient temperature from as low as about 25° C. up to about 45° C. For example, a organic-mineral hybrid sunscreen composition is considered to demonstrate stability of the emulsion structural if the organic-mineral hybrid sunscreen composition does not exhibit signs of phase separation, and/or become inhomogeneous after up to 12 weeks in an ambient temperature in the range from about 5° C. up to and including about 45° C.

The term "substantially free" or "essentially free" as used herein means that there is less than about 2% by weight of a specific material added to a composition, based on the total weight of the organic-mineral hybrid sunscreen compositions. Nonetheless, the organic-mineral hybrid sunscreen compositions may include less than about 1 wt. %, less than about 0.5 wt. %, less than about 0.1 wt. %, less than 0.01 wt. %, or none of the specified material.

The term "sun protection factor" or "SPF" is a value expressed mathematically by the ratio of the irradiation time necessary to attain the erythemogenic threshold with the UV screening agent to the time necessary to attain the erythemogenic threshold without UV screening agent. SPF generally provides information about the skin's resistance to ultraviolet B (UVB) radiation from the sun. The SPF rating system has been developed to provide consumer guidance in selecting sunscreens. The organic-mineral hybrid sunscreen composition according to the present disclosure can be formulated to achieve a variety of different SPFs. For example, the organic-mineral hybrid sunscreen composition can have an in vivo SPF of at least 30, 35, 40, 45, 50, or 55 or higher (or in a range between any of these values). As demonstrated herein, in some embodiments, the organic-mineral hybrid sunscreen composition has an SPF that is at least 50 or greater, measured as defined by FDA 2011 SPF testing method and/or on a tested subject.

The term "water-in-oil emulsion" or "W/O emulsion" includes a water phase dispersed in an oil phase, where the oil phase is a continuous phase.

The instant disclosure relates to an organic-mineral hybrid sunscreen composition and embodiments thereof which provide a high degree of sun protection, emulsion structural stability as demonstrated by macroscopic and microscopic examination, and optimized sensorial, and unique texture, the organic-mineral hybrid sunscreen composition including in the oil phase at least one mineral UV filter and a blend of organic UV filters, at least one oil solvent, at least one surfactant, and in the water phase, water, at least one water-miscible solvent, one or more skin actives, a water soluble polymer, the organic-mineral hybrid sunscreen composition also including at least one filler. The organic-minder hybrid sunscreen composition is characterized by a solvent ratio in oil phase of solvent:total oil phase of less than or equal to 5%.

The inventors surprisingly found that by decreasing the amount of solvent in the lipid phase as compared with a benchmark comparative composition wherein the solvent is typically is relied on to disperse the UV filter, and adding a filler, they were able to increase the SPF of the formula and provide a composition with a thick creamy texture that is appreciated by customers. Varied comparative examples demonstrate that the same formula as the inventive without the filler and/or with more solvents doesn't reach SPF 30 and does not satisfy critical wavelength requirements. Further, as compared with the benchmark comparative composition, the inventive composition demonstrates improved stability based on macroscopic and microscopic emulsion examination at varying conditions robust.

The inventors have discovered that in the organic-mineral hybrid sunscreen composition with high UV filters (for example, in th exemplified inventive composition having 22% organic filters and 8% mineral filter) with an amount of solvent in the lipid phase that is at or less than 5% by weight of the oil phase, and inclusion of a filler, the SPF of the formula is maintained at or greater than SPF 30 with an unexpectedly thick creamy texture that provides a rich skin finish appreciated by customers. Comparative examples demonstrate that higher amounts of oil phase solvent (greater than 5% by weight of the oil phase) and removal of the filler, even with the same quantity of UV filters, results in significantly reduced SPF.

The organic-mineral hybrid sunscreen composition demonstrates emulsion structural stability wherein the sunscreen composition does not exhibit signs of phase separation, and/or become inhomogeneous after up to 12 weeks in an ambient temperature in the range from about 5° C. up to and including about 45° C., and maintains emulsion structural stability, with minimal color change at 60° C. for at least one week. In the various embodiments, the organic-mineral hybrid sunscreen composition demonstrates an SPF of about 30 and CWL of at least 370 nm.

In the exemplified embodiments, the organic-mineral hybrid sunscreen composition is free from or devoid of organic UV filters selected from menthyl anthranilate (meradimate), parabens or a combination thereof.

UV Filters

In accordance with the various embodiments, the organic-mineral hybrid sunscreen composition according to the disclosure includes at least one inorganic/mineral based UV filter and a blend of organic UV filters present in the oil phase of the emulsion.

In particular, the organic-mineral hybrid sunscreen composition includes zinc oxide and a combination of organic UV filters comprising octinoxate (ethylhexyl methoxycinnamate), octisalate (ethylhexyl salicylate), octocrylene, and homosalate.

In some particular embodiments, the organic-mineral hybrid sunscreen composition excludes, or is free from or devoid of organic UV filters comprising menthyl anthranilate (meradimate). In some particular embodiments, the organic-mineral hybrid sunscreen composition excludes, or is free from or devoid of organic UV filters selected from oxybenzone and octinoxate organic UV filters.

In various embodiments of the organic-mineral hybrid sunscreen composition, the zinc oxide UV filter is present in an amount in an amount of about 8% weight of the organic-mineral hybrid sunscreen composition, octinoxate (ethylhexyl methoxycinnamate) present in an amount in the range from about 1% to about 8%, or at about 5%, octisalate (ethylhexyl salicylate) is present in an amount in the range from about 1% to about 7%, %, or at about 5%, octocrylene present in an amount in the range from about 0.5% to about 5%, or at about 2%, and homosalate is present in an amount in the range from about 5% to about 15%, or at about 10%, and each present by weight based on the total weight of the organic-mineral hybrid sunscreen composition. Thus, an organic UV filter may be present in the organic-mineral hybrid sunscreen composition, alone as described herein above, or as combined, by weight, based on the total weight of the organic-mineral hybrid sunscreen composition, from about 0.5, 1, 2, 3, 4, 6, 7, 8, 9, 10, 11, 12, 13, 14, 15, 16, 17, 18, 19, 20, 21, 22, 23, 24 to about 25 weight percent, including increments and ranges therein and there between.

Oil

In accordance with the various embodiments, the organic-mineral hybrid sunscreen composition includes any one or a combination of cosmetic oils. In some embodiments, the oil is generally immiscible in water.

In some embodiments the oil is a silicone oil. In some particular embodiments, the oil comprises dimethicone.

The oil may be selected from silicones, hydrocarbons, fatty alcohols, glycols, and vegetable oils. The oil may include one or a combination of polar and non-polar oil. In some embodiments, the oil may be chosen from hydrocarbon-based oils from plants or of plant origin, mineral oil, ester oils, fatty alcohols containing from 12 to 26 carbon atoms, fatty acids containing from 12 to 26 carbon atoms and vinylpyrrolidone copolymers, and combinations thereof.

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil, or a synthetic hydrocarbon-based oil. Further, suitable oil may be a mineral hydrocarbon-based oil, a plant hydrocarbon-based oil, or a synthetic hydrocarbon-based oil.

Silicone Oils

The organic-mineral hybrid sunscreen composition may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the organic-mineral hybrid sunscreen composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent or at the end of the silicone chain, which groups each contain from 2 to 24 carbon atoms, or phenyl silicones, such as phenyl trimethicones, phenyl dimethicones, phenyl (trimethylsiloxy)diphenylsiloxanes, diphenyl dimethicones, diphenyl(methyldiphenyl)trisiloxanes or (2-phenylethyl) trimethylsiloxysilicates.

Other examples of silicone oils that may be mentioned include volatile linear or cyclic silicone oils, especially those with a viscosity 8 centistokes (8×106 m2/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, hepta methyloctyltrisiloxane, hexamethyldisiloxane, octamethyltrisiloxane, decamethyltetrasiloxane and dodecamethylpentasiloxane, and mixtures thereof.

Fluoro Oils

The organic-mineral hybrid sunscreen composition may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The organic-mineral hybrid sunscreen composition may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the organic-mineral hybrid sunscreen composition may include a synthetic oil selected from the group consisting of hydrogenated polyisobutene and hydrogenated polydecene. A hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from C4 to C24, it being possible for these chains to be saturated or unsaturated and linear or branched; these oils are in particular wheat germ oil, sunflower oil, grape seed oil, sesame oil, corn oil, apricot oil, castor oil, rhea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 40 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ÿ 10, for instance Purcellin oil (cetearyl octanoate), isopropyl myristate, isopropyl palmitate, C12-C15 alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear C12-C13 alkyl) tartrates, such as those sold under the name Cosmacol ETI® by Enichem Augusta Industriale, and also di(linear C14-C15 alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid, or linolenic acid;

(vii) carbonates, such as dicaprylyl carbonate, such as the product sold under the name Cetiol CC™ by Cognis;

(viii) fatty amides, such as isopropyl N-lauroyl sarcosinate, such as the product sold under the trade name Eldew SL 205™ from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

Hydrocarbon-based oils may be glyceride triesters and in particular to caprylic/capric acid triglycerides, synthetic esters and in particular isononyl isononanoate, oleyl erucate, C12-C15 alkyl benzoate, 2-ethylphenyl benzoate and fatty alcohols, such as octyldodecanol. As volatile hydrocarbon-based oils, mention is made of hydrocarbon-based oils containing from 8 to 16 carbon atoms and in particular of branched C8-C16 alkanes, such as C8-C16 isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C C8-C16 esters, and isohexyl neopentanoate.

In some embodiments, the organic-mineral hybrid sunscreen composition may comprise one or more oils such as from those described herein above, and from oils that may be selected from branched or linear, liquid alkane with carbon chain length of C11 to C20. In various embodiments, liquid alkanes may be selected from those with a carbon chain length of from C11 to C20. The liquid alkanes may be selected from those with a carbon chain length of from C11 to C20, or from C15 to C19, or one of C11, C12, C13, C14, C15, C16, C17, C18 to C19. In some embodiments, suitable liquid alkanes that may be used according to the disclosure include hydrocarbon-based oils containing from 8 to 16 carbon atoms, and especially branched C8-C16 alkanes such as C8-C16 isoalkanes.

In some embodiments, the organic-mineral hybrid sunscreen composition may comprise one or more oils selected from polar emollients selected from esters, triglycerides, ethers, carbonates, alcohols, oils, butters, fatty acids, and their combinations thereof. In various embodiments, the polar emollients may be selected from those with a molecular weight of 400 g/mol or less. More, generally, the polar emollient may have a molecular weight in the range from about 50 g/mol % to about 350 g/mol.

In some embodiments, the organic-mineral hybrid sunscreen composition may comprise polar emollients that include those derived from C12-050 fatty acids, preferably C16-C22 saturated fatty acids, and monohydric alcohols. In some embodiments, such esters may be chosen from isopropyl myristate, methyl palmitate, isopropyl laurate, isopropyl palmitate, ethylhexyl palmitate, ethylhexyl laurate, ethylhexyl oleate, ethylhexyl isononanoate, myristyl myristate, 2-ethylhexyl caprate/caprylate (or octyl caprate/caprylate), 2-ethylhexyl palmitate, isostearyl neopentanoate, isononyl isononanoate, hexyl laurate, esters of lactic acid and of fatty alcohols comprising 12 or 13 carbon atoms, dicaprylyl carbonate and their mixtures.

The one or more oil, alone or in combination as a blend of oils, may be present in the organic-mineral hybrid sunscreen composition from about 0.0001% to about 10% or from about 0.001% to about 0.010%, or from about 0.01% to about 0.1%, or from about 0.1% to about 10%, or from about 0.5% to about 20%, or from about 1% to about 10%, or from about 5% to about 10%, or from about 1% to about 3%, or from about 1% to about 2%, or any suitable combination, sub-combination, range, or sub-range thereof by weight, based on the weight of the organic-mineral hybrid sunscreen composition. One of ordinary skill in the art, however, will appreciate that other ranges are within the scope of the invention. In some embodiments, the organic-mineral hybrid sunscreen composition includes more than one oil, each oil present in an amount as set forth herein above, wherein each different oil (such as, for example, plant oils and extracts with oils) may be present within one of the ranges selected from the ranges set forth herein above.

Thus, each of the at least one oil or combination of oils is present by weight, based on the total weight of the organic-mineral hybrid sunscreen composition, from about 0.0001, 0.001, 0.01, 0.1, 1.0, 1.1, 1.2, 1.3, 1.4, 1.5, 1.6, 1.7, 1.8, 1.9, 2, 3, 4, 5, 6, 7, 8, 9, to about 10 percent, including increments and ranges therein and there between.

Surfactant

In various embodiments, the organic-mineral hybrid sunscreen composition comprises at least one surfactant.

In some embodiments, surfactants may be selected from the group consisting of cationic surfactants comprising quaternary ammonium compounds, in some embodiments comprising a quaternary ammonium salt and a fatty alcohol and combinations thereof.

In some particular embodiments, the organic-mineral hybrid sunscreen composition comprises at least one surfactant comprising cetearyl alcohol (and) behentrimonium methosulfate.

Non-limiting examples of cationic surfactants include behentrimonium methosulfate, behentrimonium chloride, cetrimonium chloride, stearimonium chloride, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethyla mine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

In some embodiments, cetearyl alcohol (and) behentrimonium methosulfate is present from about 0.1% to about 10%, or at about 0.8% to about 6%, or about 4% to about 5%, or about 4.5%, all amounts by weight based on the total weight of the organic-mineral hybrid sunscreen composition.

Each one of the at least one surfactant is present in the organic-mineral hybrid sunscreen composition at a concentration from about 0.1% to about 10%, or from about 0.2% to 10%, or from about 1% to 5% by weight, all weights based on the total weight of the organic-mineral hybrid sunscreen composition. Thus, in various embodiments, each one or a combination of surfactants is present in the organic-mineral hybrid sunscreen composition in a weight percent amount from 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, to about 10 percent by weight, including increments there between.

Polymer

In various embodiments, the organic-mineral hybrid sunscreen composition comprises at least one polymer. In some embodiments the at least one polymer is selected from the group consisting of celluloses, gums, hydrophilic colloids, and combinations thereof.

Polymers may be selected from the group consisting of nonionic, anionic, cationic, and amphoteric polymers, such as polysaccharides that include chitosan, chitin, starches, alginates, celluloses, galactomannans such as guar gums and its derivatives, including hydroxypropyl guar, cationic guar derivatives, gums of microbial origin, including xanthan gum, scleroglucan gum, mucopolysaccharides, chondroitin sulfates, and mixtures thereof, and gums derived from plant exudates, including locust bean gums, gum arabic, ghatti gum, karaya gum, gum tragacanth, carrageenan gum, agar gum and carob gum, cellulose-based polymers, including methylcellulose, hydroxyalkylcellulose, ethylhydroxyethylcelluloses, hydroxyethylcellulose, hydroxypropylcellulose, carboxymethylcellulose, cationic cellulose ether derivatives, quaternized cellulose derivatives, nitrocellulose, hemicellulose and hemicellulose derivatives, mannans, xylans, lignins, arabans, galacturonans, alginate-based compounds, glucuronoxylans, arabinoxylans, xyloglucans, glucomannans, fructosans such as inulin, pectic acids and pectins, arabinogalactans, agars, glycosaminoglycans, gelatin, gellan, crosslinked homopolymers of acrylic acid, and combinations thereof.

In some particular embodiments, the organic-mineral hybrid sunscreen composition comprises at least one polymer comprising hydroxyethylcellulose.

The at least one polymer present in the organic-mineral hybrid sunscreen composition according to the disclosure from about 0.01% to about 10% by weight, or from about 0.05% to about 5% by weight, or from about 0.1% to about 2%, or about 0.5%, or any suitable combination, sub-combination, range, or sub-range thereof by weight, based on the weight of the organic-mineral hybrid sunscreen composition.

Thus, one or a combination of polymers may be present, by weight, based on the total weight of the organic-mineral hybrid sunscreen composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, to about 10 weight percent, including increments and ranges therein and there between.

Filler

In accordance with various embodiments, the organic-mineral hybrid sunscreen composition comprises one or more fillers. The fillers may be of mineral or organic origin, natural or synthetic in nature, and in some examples are selected from oil absorption or optical effect fillers. Oil absorption fillers may impart a matte effect and non-greasy feeling onto the skin. Optical effects fillers may impart a soft-focus/haze/blur effect to the skin, provide the skin with a more uniform appearance, reduce the appearance of skin imperfections or discoloration, or reduce the visibility of pores.

In some embodiments according to the disclosure, a filler may include one or more of starches, salts and combinations thereof.

In some particular embodiments according to the disclosure, a filler may include aluminum starch octenylsuccinate.

Some examples of oil-absorbing fillers include: aluminum starch octenylsuccinate, mica, zea may (corn) starch, magnesium oxide, nylon-12, nylon-66, cellulose, polyethylene, talc, talc (and) methicone, talc (and) dimethicone, perlite, sodium silicate, pumice, PTFE, Ammonium Polyacryloyldimethyl Taurate, polymethyl methacrylate, *Oryza sativa* (rice) starch, potato starch modified, alumina, calcium sodium borosilicate, magnesium carbonate, hydrated silica, dimethicone/vinyl dimethicone crosspolymer, sodium carboxymethyl starch. According to one preferred embodiment, the oil-absorbing filler comprises spherical microparticles of porous silica having a mean particle size from 0.5 to 20 μm whose INCI name is silica sold by the company JCG Catalysts and Chemicals under the name Spheron L-1500. According to another preferred embodiment, the oil absorbing filler comprises hydrophobic aerogel particles whose INCI name is silica silylate sold by Dow Corning under the name VM-2270 Aerogel Fine Particles.

Some examples of optical effects fillers include: bismuth oxychloride, silica silylate, boron nitride, iron oxide, calcium carbonate, calcium sulfate (and) iron oxides, sodium potassium aluminum silicate.

Some examples of fillers which provide both oil-absorbing and optical effects include: silica, silica (and) methicone, silica (and) dimethicone, polysilicone-22, polysilicone-8, polysilicone-11, methyl methacrylate crosspolymer, polymethylsilsesquioxane, methylsilanol/silicate crosspolymer, vinyl dimethicone/methicone silsesquioxane crosspolymer, diphenyl dimethicone/vinyl diphenyl dimethicone silsesquioxane crosspolymer, and styrene/acrylates copolymer.

The filler may be present in the organic-mineral hybrid sunscreen composition according to the invention, at a concentration, or from about 0.01% to 10%, or from about 0.01% to 5%, or from about 0.1% to 1%, or from about 0.2% to 0.8%, or from about 0.3% to 0.4%, or about 0.5%, or any suitable combination, sub-combination, range, or sub-range thereof by weight, based on the weight of the organic-mineral hybrid sunscreen composition. One of ordinary skill in the art, however, will appreciate that other ranges are within the scope of the invention. In some embodiments, the organic-mineral hybrid sunscreen composition includes more than one filler, each filler present in an amount as set forth herein above, wherein each different filler may be present within one of the ranges selected from the ranges set forth herein above.

Thus, each one or combination of filler may be present by weight, based on the total weight of the organic-mineral hybrid sunscreen composition, from about 0.01, 0.02, 0.03, 0.04, 0.06, 0.07, 0.08, 0.09, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, to about 10 percent by weight, including increments and ranges there between.

Water

In accordance with the various embodiments, the organic-mineral hybrid sunscreen composition includes water.

In various embodiments, the organic-mineral hybrid sunscreen composition comprises from about 40% to about 70% water, and in some embodiments from about 45% to about 50% water, including increments and all ranges and subranges therein and there between, by weight, based on the total weight of the organic-mineral hybrid sunscreen composition. One of ordinary skill in the art, however, will appreciate that other ranges are within the scope of the invention. Thus, water is present, by weight, based on the total weight of the organic-mineral hybrid sunscreen composition, from about 40, 45, 50, 55, 60, 65, 66, 67, 68, 69, to about 70 weight percent, including increments and all ranges and subranges therein and there between.

The water used in the organic-mineral hybrid sunscreen composition may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

Water-Soluble Solvents

In accordance with various embodiments, the organic-mineral hybrid sunscreen composition includes at least one water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some embodiments, the water-soluble solvent has a solubility of at least 60%, 70%, 80%, or 90% in water under these conditions. Non-limiting examples of water-soluble solvents include, for example, glycerin, alcohols (for example, C1-C30, C1-C15, C1-C10, or C1-C4 alcohols), organic solvents, polyols, glycols, or combinations thereof.

In some embodiments, a water-soluble solvent is selected from the group consisting of inferior alcohols, diols, polyols, and combinations thereof. In some embodiments, the water-soluble solvent may be propylene glycol, butylene glycol, glycerin, or a combination thereof.

In some particular embodiments according to the disclosure, the water-soluble solvent is selected from the group consisting of glycerin, propanediol, and a combination thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propanediol, and glycerin. The organic solvents can be volatile or non-volatile compounds.

Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylene glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, or combinations thereof.

In accordance with the various embodiments the amount of the at least one water-soluble solvent, when present, is from about 1% to about 20%, or from about 1% to about 10%, or from about 2% to about 8%, or about 3%, or any suitable combination, sub-combination, range, or sub-range thereof by weight, based on the weight of the organic-mineral hybrid sunscreen composition. One of ordinary skill in the art, however, will appreciate that other ranges are within the scope of the invention. In some embodiments, the organic-mineral hybrid sunscreen composition includes more than one water soluble solvent, each water-soluble solvent present in an amount as set forth herein above, wherein each different water-soluble solvent may be present within one of the ranges selected from the ranges set forth herein above.

Thus, each one or combination of water-soluble solvents is present by weight, based on the total weight of the organic-mineral hybrid sunscreen composition, from about 1, 2, 3, 4, 5, 6, 7, 8, 9, 10, 11, 12, 13, 14, 15, 16, 17, 18, 19 to about 20 weight percent, including increments and ranges therein and there between.

Other Ingredients

In accordance with various embodiments, the organic-mineral hybrid sunscreen composition according to the disclosure includes one or more ingredients.

SPF Boosters

In accordance with some embodiments, the organic-mineral hybrid sunscreen composition according to the disclosure may comprise one or a combination of SPF boosters. In accordance with some embodiments, the organic-mineral hybrid sunscreen composition according to the disclosure excludes SPF boosters.

In some embodiments, the SPF booster is selected from Butyloctyl Salicylate, ethylhexyl methoxycrylene, styrene/acrylates copolymer (such as the product sold under the tradename SUNSPHERES™), Ethylenediamine/Stearyl Dimer Dilinoleate Copolymer, Dimethicone and Acrylates/Dimethicone Copolymer, silicone polymer comprising dimethicone (and) dimethicone/vinyl dimethicone copolymer, the UVA booster Solastay, and combinations thereof. In some particular embodiments, the SPF booster comprises Butyloctyl Salicylate.

The one or combination of SPF boosters, when present, may be at a concentration from about 0.01% to 25%, in some embodiments from about 0.1% to 13%, and in some embodiments from about 0.5% to 10%, and in some embodiments from about 1% to 5%, or about 3% by weight, all weights based on the total weight of the organic-mineral hybrid sunscreen composition. Thus, in various embodiments, an SPF booster, when present, may be present in a composition in a weight percent amount from 0.01, 0.02, 0.03, 0.04, 0.05, 0.06, 0.07, 0.08, 0.09, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0 to 25.0 percent by weight, including increments there between.

Cosmetic Waxes

In accordance with the disclosure, optionally one or more wax may be present in the organic-mineral hybrid sunscreen composition, the wax selected from natural and synthetic waxes. Natural waxes can include animal tallow, bayberry wax, beeswax, grapefruit wax, orange peel wax, palm wax, rice bran wax, sumac wax, sunflower wax, soy wax, polyhydroxystearic acid, and combinations thereof.

In some embodiments, when present, a wax may be selected from *Oryza sativa cera* (rice bran wax), candelilla wax, sunflower seed wax, carnauba wax, polyhydroxystearic acid, and combinations thereof. In a particular embodiment, the organic-mineral hybrid sunscreen composition comprises rice bran wax.

In accordance with the various embodiments, the one or wax, when present, is present in the organic-mineral hybrid sunscreen composition at a concentration, by weight, of between about 0.1% to about 10%, or from about 0.2% to about 4%, or from about 0.5% to about 3%, or from about 1% to about 2%, or any suitable combination, sub-combination, range, or sub-range thereof by weight, based on the weight of the organic-mineral hybrid sunscreen composition.

In some embodiments, the organic-mineral hybrid sunscreen composition comprises a more than one wax, each one present in the organic-mineral hybrid sunscreen composition at a concentration, by weight, based on the total weight of organic-mineral hybrid sunscreen composition, in the range from about 0.1% to about 10%, or any suitable combination, sub-combination, range, or sub-range thereof by weight, based on the weight of the organic-mineral hybrid sunscreen composition.

Thus, when present, the wax is present by weight, based on the total weight of the organic-mineral hybrid sunscreen composition from about 0.10, 0.20, 0.30, 0.40, 0.50, 0.60, 0.80, 0.90, 1.0, 2, 3, 4, 5, 6, 7, 8, 9, to about 10 weight percent, including increments and ranges therein and there between.

Powders

In accordance with some embodiments, the organic-mineral hybrid sunscreen composition according to the disclosure may optionally comprise one or a combination of powders comprising sensorial feel modifying powders. In some particular embodiments, the powders may be selected from boron nitride, perlite, and aluminium starch octenyl succinate.

The one or combination of powders, when present, may be at a concentration from about 0.05% to 15%, in some embodiments from about 0.1% to 10%, and in some embodiments from about 1% to 5% by weight, all weights based on the total weight of the organic-mineral hybrid sunscreen composition. Thus, in various embodiments, a powder, when present, may be present in a composition in a weight percent amount from 0.05, 0.06, 0.07, 0.09, 1.0, 2.0, 3.0, 4.0, 5.0, 6.0, 7.0, 8.0, 9.0, 10.0, 11.0, 12.0, 13.0, 14.0, to 15.0 percent by weight, including increments there between.

Actives/Other Additives

The organic-mineral hybrid sunscreen compositions can also comprise one or a combination of actives or optional additives used in the cosmetics field which does not affect the properties of the organic-mineral hybrid sunscreen compositions according to the invention, such as fragrances, dyes, pearlescent agents, silica, preservatives, proteins, protein hydrolysates, ceramides, antioxidants, vitamins (for example, Vitamin C, B vitamins, Vitamin E, Vitamin A, Vitamin D, and derivatives, provitamins, and vitamers thereof, including but not limited to ascorbic acid, panthenol, tocopherol, tocotrienol, retinol, calciferol), silicones, odor absorbers and coloring materials; anti-microbial components, including, but not limited to, phenoxyethanol, chlorphenesin, capryloyl glycol and sodium salicylate; essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang; fruit extracts, for example *Pyrus Malus* (Apple) Fruit Extract, and Aloe Barbadensis Leaf Juice Powder; citric acid, sodium chloride; neutralizing or pH-adjusting agents (e.g., triethylamine (TEA) and sodium hydroxide), and combinations thereof. Ceramides may include ceramide complex, a ceramide blend that includes Ceramide NP, Ceramide AP and Ceramide EOP (for example, SK-IN-FLUX™ from Evonik).

Although the actives/optional additives are given as examples, it will be appreciated that other optional components compatible with cosmetic applications known in the art may be used.

In some embodiments, the organic-mineral hybrid sunscreen composition may include one or a combination of trisodium ethylenediamine disuccinate, hydroxyacetophenone, sodium hyaluronate, hydrolyzed hyaluronic acid, ceramides, phenoxyethanol, niacinamide, diethylhexyl syringylidenemalonate, citric acid, EDTA, propylparaben, methylparaben, panthenol, tocopherol, and combinations thereof.

In some particular embodiments, the organic-mineral hybrid sunscreen composition comprises trisodium ethylenediamine disuccinate, hydroxyacetophenone, sodium hyaluronate, hydrolyzed hyaluronic acid, ceramides, niacinamide, and combinations thereof.

In accordance with the various embodiments, the amount of each one or a combination of actives/optional additives, when present in the organic-mineral hybrid sunscreen composition can be present in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2.5% by weight, or from about 1% to about 2%, or any suitable combination, sub-combination, range, or sub-range thereof by weight, based on the total weight of the organic-mineral hybrid sunscreen composition. And in some embodiments, a combination of actives present in the organic-mineral hybrid sunscreen composition can be present in a range from about 0.001% to about 20%.

Thus, any one or a combination of actives/optional additives, when present, may be present, by weight, based on the total weight of the organic-mineral hybrid sunscreen composition, each one or the combination present from about 0.001, 0.002, 0.003, 0.004, 0.005, 0.007, 0.008, 0.009, 0.01, 0.02, 0.03, 0.04, 0.05, 0.06, 0.07, 0.08, 0.09, 0.10, 0.20, 0.30, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

The instant disclosure also relates to methods for protecting skin from UV radiation comprising applying an effective amount of the organic-mineral hybrid sunscreen composition of claim 1 to the skin.

EXAMPLES

The following Examples are provided for illustrative purposes only and are not intended to be limiting.

Example 1: Raw Materials

Selected raw materials as used in the organic-mineral hybrid sunscreen composition are identified in the table below.

TABLE 1

| Representative Raw Materials | |
|---|---|
| Raw Material | Percent Active |
| ZnO (Z-COTE HP1 (TM)) | ~98% ZnO active |
| Octocrylene | ~100% |
| Homosalate | ~100% |
| Octinoxate | ~100% |

TABLE 1-continued

| Representative Raw Materials | |
|---|---|
| Raw Material | Percent Active |
| Octisalate | ~100% |
| Aluminum Starch Octenylsuccinate | ~100% |
| Dimethicone | ~100% |

Example 2: Inventive, Base and Comparative Compositions

An organic-mineral hybrid sunscreen composition according to the disclosure was prepared and which has demonstrated physical and chemical properties as described herein below. The inventive composition was evaluated by an FDA Method in vivo SPF characterization, achieving a value of 30 or higher, and demonstrates stability and sensorial properties, as described herein. The compositions are each described in the Tables 2-5 below.

TABLE 2

| Inventive Example | | |
|---|---|---|
| Ingredient | Phase | INVENTIVE |
| ORGANIC UV FILTERS (ETHYLHEXYL METHOXYCINNAMATE/ OCTINOXATE (~5%), ETHYLHEXYL SALICYLATE (~5%), OCTOCRYLENE (~2%), HOMOSALATE (~10%)) | OIL | ~22 |
| OIL PHASE SOLVENT (DIMETHICONE) | OIL | ~2 |
| MINERAL UV FILTER (ZINC OXIDE*) | OIL | ~8.21 |
| SURFACTANT (CETEARYL ALCOHOL (and) BEHENTRIMONIUM METHOSULFATE) | OIL | ~4.5 |
| OTHER ADDITIVES/ PRESERVATIVES (TRISODIUM ETHYLENEDIAMINE DISUCCINATE, HYDROXYACETOPHENONE, PHENOXYETHANOL) | WATER | ~1 |
| SKIN ACTIVES (SODIUM HYALURONATE, CERAMIDE BLEND, NIACINAMIDE) | WATER | ~5 |
| FILLER (ALUMINUM STARCH OCTENYLSUCCINATE) | | ~0.5 |
| POLYMER (HYDROXYETHYLCELLULOSE) | WATER | ~0.5 |
| WATER PHASE SOLVENT (GLYCERIN, PROPANEDIOL) | WATER | ~6 |
| WATER | WATER | ~50.5 (QS) |
| Weight Ratio UV Filter:Oil Phase | | =~0.82 |
| Weight Ratio Oil Phase Solvent: Oil Phase (</=5%) | | =~0.05 |

*ZnO RM; final active is ~8%

TABLE 3

| Comparative Composition | | |
|---|---|---|
| Ingredient | Phase | COMPARATIVE |
| ORGANIC UV FILTERS (ETHYLHEXYL METHOXYCINNAMATE (~5%), MENTHYL ANTHRANILATE (MERADIMATE) (~5%), OCTOCRYLENE (~2%), HOMOSALATE (~10%)) | OIL | ~22 |
| OIL PHASE SOLVENT (DIMETHICONE) | OIL | ~1 |
| MINERAL UV FILTER (ZINC OXIDE*) | OIL | ~6.46 |
| SURFACTANT (CETEARYL ALCOHOL (and) BEHENTRIMONIUM METHOSULFATE) | OIL | ~4 |

TABLE 3-continued

Comparative Composition

| Ingredient | Phase | COMPARATIVE |
|---|---|---|
| OTHER ADDITIVES/PRESERVATIVES (DISODIUM EDTA, METHYLPARABEN, PROPYLPARABEN) | WATER | ~0.5 |
| SKIN ACTIVES (HYDROLYZED HYALURONIC ACID, CERAMIDE BLEND, NIACINAMIDE) | WATER | ~4.8 |
| FILLER (ALUMINUM STARCH OCTENYLSUCCINATE) | | ~0.5 |
| POLYMER (HYDROXYETHYLCELLULOSE) | WATER | ~0.5 |
| WATER PHASE SOLVENT (GLYCERIN) | WATER | ~3 |
| WATER | WATER | ~58 (QS) |
| Weight Ratio UV Filter:Oil Phase | | =~0.85 |
| Weight Ratio Oil Phase Solvent:Oil Phase (</=5%) | | =~0.03 |

*ZnO RM; final Zn active is ~8%

TABLE 4

Base Composition (for Varied Compositions)

| Ingredient | INVENTIVE |
|---|---|
| ORGANIC UV FILTERS (ETHYLHEXYL METHOXYCINNAMATE/OCTINOXATE, ETHYLHEXYL SALICYLATE, OCTOCRYLENE, HOMOSALATE) | Varied |
| OIL PHASE SOLVENT (DIMETHICONE) | Varied |
| MINERAL UV FILTER (ZINC OXIDE) | Varied |
| SURFACTANT (CETEARYL ALCOHOL (and) BEHENTRIMONIUM METHOSULFATE) | ~4.5 |
| OTHER ADDITIVES/PRESERVATIVES (TRISODIUM ETHYLENEDIAMINE DISUCCINATE, HYDROXYACETOPHENONE, PHENOXYETHANOL) | ~1 |
| SKIN ACTIVES (SODIUM HYALURONATE, CERAMIDE BLEND, NIACINAMIDE) | ~5 |
| FILLER (ALUMINUM STARCH OCTENYLSUCCINATE) | Varied |
| POLYMER (HYDROXYETHYLCELLULOSE) | Varied |
| WATER PHASE SOLVENT (GLYCERIN, PROPANEDIOL) | ~6 |
| WATER | Varied (QS) |

The foregoing Base composition was used to provide each of Comparative Compositions listed in Table 5, below (identified as VAR 1-VAR 15).

TABLE 5

Varied Compositions (Comparatives) based on Inventive Base Composition

| Composition | Filter System | Other Varied Ingredients |
|---|---|---|
| INVENTIVE | 10% Homosalate<br>5% Octinoxate<br>5% Octisalate<br>2% Octocrylene<br>8% ZnO | NA |
| VAR 1 | 10% Homosalate<br>5% Octisalate<br>7% Octocrylene<br>6.3% ZnO | ~2% Glyceryl Stearate (And) Peg-100 Stearate<br>~4% Cetearyl Alcohol (And) Behentrimonium Methosulfate (Decreased)<br>~5% Cetearyl Alcohol (And) Ceteareth-20 |
| VAR 2 | 15% Homosalate<br>5% Octisalate<br>7% Octocrylene<br>6.3% ZnO | ~0.4% Hydroxyethyl Acrylate/Sodium Acyloyldimethyl Taurate Copolymer<br>~3% Caprylyl Methicone<br>~2% Glyceryl Stearate (And) Peg-100 Stearate<br>~4 (Decreased)<br>~5% Cetearyl Alcohol (And) Ceteareth-20 |
| VAR 3 | 10% Homosalate<br>5% Octinoxate<br>3% Octisalate<br>2% Octocrylene<br>8% ZnO | ~0.4% Hydroxyethyl Acrylate/Sodium Acyloyldimethyl Taurate Copolymer<br>~3% Caprylyl Methicone |
| VAR 4 | 10% Homosalate<br>5% Octinoxate<br>5% Octocrylene<br>8% ZnO | ~4% Cetearyl Alcohol (And) Behentrimonium Methosulfate (Decreased) |
| VAR 5 | 10% Homosalate<br>5% Octisalate<br>7% Octocrylene<br>8% ZnO | ~4% Cetearyl Alcohol (And) Behentrimonium Methosulfate (Decreased) |
| VAR 6 | 10% Homosalate<br>5% Octinoxate<br>7% Octocrylene<br>8% ZnO | ~4% Cetearyl Alcohol (And) Behentrimonium Methosulfate (Decreased)<br>~3% Dimethicone (Increased) |
| VAR 7 | 10% Homosalate<br>5% Octisalate<br>7% Octocrylene<br>8% ZnO<br>(+3% BOS) | Includes Spf Booster<br>~4% Cetearyl Alcohol (And) Behentrimonium Methosulfate (Decreased)<br>~3% Dimethicone (Increased) |
| VAR 8 | 13% Homosalate<br>5% Octisalate<br>7% Octocrylene<br>8% ZnO | ~4% Cetearyl Alcohol (And) Behentrimonium Methosulfate (Decreased)<br>~3% Dimethicone (Increased) |
| VAR 9 | 10% Homosalate<br>5% Octinoxate<br>7% Octocrylene<br>8% ZnO<br>(+3% BOS) | Includes Spf Booster |
| VAR 10 | 13% Homosalate<br>5% Octinoxate<br>7% Octocrylene<br>8% ZnO | ~4.25% Cetearyl Alcohol (And) Behentrimonium Methosulfate (Decreased)<br>~3% Dimethicone (Increased)<br>0% Filler (Decreased) |
| VAR 11 | 10% Homosalate<br>5% Octinoxate<br>5% Octisalate<br>2% Octocrylene<br>8% ZnO | ~3.5% Dimethicone (Increased)<br>~4.25% Cetearyl Alcohol (And) Behentrimonium Methosulfate (Decreased)<br>0% Filler (Decreased)<br>Weight Ratio UV Filter:Oil Phase = ~0.79;<br>Weight Ratio Oil Phase Solvent:Oil Phase (</=5%) = ~0.09 |
| VAR 12 | 12% Homosalate<br>5% Octinoxate<br>5% Octisalate<br>8% ZnO | Includes Spf Booster<br>~4.25% Cetearyl Alcohol (And) Behentrimonium Methosulfate (Decreased)<br>~3.5% Dimethicone (Increased)<br>0% Filler (Decreased) |
| VAR 13 | 13% Homosalate<br>5% Octinoxate<br>5% Octisalate<br>8% ZnO | ~4.25% Cetearyl Alcohol (And) Behentrimonium Methosulfate (Decreased)<br>~3.5% Dimethicone (Increased)<br>0% Filler (Decreased)<br>~0.5% Dicaprylyl Ether |

Note:
ZnO amounts are final active, not amount of RM

Example 3: SPF and Critical Wavelength (CWL) Tests with Inventive and Comparative Compositions Each of the Inventive and Comparative Compositions were evaluated for SPF and CWL. As shown in Table 6, below, passing compositions demonstrated a stable SPF of >/=30 and a CWL of >/=370 nm.

TABLE 6

SPF and CWL Results

| Composition | SPF | Critical Wavelength ($\lambda_c$) | Pass/Fail |
|---|---|---|---|
| INVENTIVE | 31 | 370.1 nm | Pass |
| COMPARATIVE | 30 | 370.1 nm | Pass |
| VAR 1 | ND | 369.4 nm | Fail |
| VAR 2 | ND | 368.3 nm | Fail |
| VAR 3 | 16 | 370.1 nm | Fail |
| VAR 4 | 16 | 370.6 nm | Fail |
| VAR 5 | 28 (std. deviation too high to achieve SPF 30) | 370.9 nm | Fail |
| VAR 6 | 15 | 370.6 nm | Fail |
| VAR 7 | 17 | 373.4 nm | Fail |
| VAR 8 | 17 | 373.2 nm | Fail |
| VAR 9 | 28 | 373.3 nm | Fail |
| VAR 10 | 21 | 373.2 nm | Fail |
| VAR 11 | 25.42 (std. deviation too high to achieve SPF 30) | ND | Fail |
| VAR 12 Octocrylene-free | 20 | 376.7 nm | Fail |
| VAR 13 Octocrylene-free | 21 | 375.4 nm | Fail |

It is apparent that the inventive composition demonstrates a 30 SPF and passing CWL while variations in the nature and amount of UV agents, amount of oil phase solvent (dimethicone) and inclusion or exclusion of filler (aluminum starch octenylsuccinate) affected one or both of SPF and CWL.

Example 4: Emulsion Structural Stability of Inventive and Comparative Compositions A panel of compositions were tested for SPF and emulsion structural stability and processability. The results are shown in Table 7, below.

TABLE 7

Stability Results for Inventive vs Comparative

| Tested Stability Conditions | INVENTIVE | COMPARATIVE |
|---|---|---|
| Stability at 1 week @ 60° C. (naked eye) | Modest color shift of emulsion; no syneresis (pooling of oil) | Noticeable color shift of emulsion; visible surface syneresis |
| Stability at 1 week @ 60° C. (microscopic) | Emulsion homogenous, tight edges | Emulsion modest inhomogeneity, loose edges |
| 8 week samples at 5° C., 25° C., 37° C. and 45° C. | Microscopic emulsion has small particle size and homogenous | Microscopic emulsion has large and irregular particles, especially at 37° C. and 45° C. |
| 12 week samples at 5° C., 25° C., 37° C. and 45° C. | Modest color shift; all samples smooth/homogenous | Noticeable color shift; sample at 45° C. demonstrated textural change and syneresis |

According to the data collected for the inventive and comparative examples, it is apparent that the inventive composition demonstrates enhanced short and long term stability (12 weeks), the stability characterized by minimal color change even at high temperature, no textural changes, pooling of oil, and good homogeneity of the emulsion as demonstrated with and without microscopic evaluation.

Example 5: Pilling Assessments: Removing Octocrylene Increases Pilling (Negative Effect)

In a clinical study a panel of sensory experts evaluated the effects of inventive compositions in a group of 15 women, Caucasian, with normal to combination skin type. Each test panelist washes her face using a commercial cleanser. Skin equilibrates for 10 minutes. About 0.3 mL of moisturizer is dispensed and applied on ½ the face and then repeated for the other side using the same dosage applying one dot each on chin, upper lip, cheek, side of nose, temple and two dots on forehead. Moisturizer is blended until all product is absorbed then skin is evaluated for visible pilling during application and photographed; timer is set for 2 minutes. After two minutes, a series of swiping motions is applied across the skin surfaces using the back of the hand and pilling is assessed and photographed.

Table 8 shows the number of panelists experiencing pilling with each tested composition before and after pilling assessment.

TABLE 8

Pilling Test Results for Inventive vs Comparative and VAR 12 and 13

| | Test Panelists Experiencing Pilling | | | | |
|---|---|---|---|---|---|
| | COMPARATIVE | INVENTIVE | VAR 11 | VAR 12 | VAR 13 |
| Before pilling gesture | 0 | 0 | 0 | 2 | 1 |
| After pilling gesture | 6 | 7 | 6 | 11 | 11 |

As shown above, the inventive composition performs on par with comparative for pilling. In addition, the inventive has sensorial attributes that are improved over the comparative with respect to peaking on application and consistency and overall shape when initially applied, and as shown in Table 7, the inventive demonstrates better stability without compromising sensorial benefits.

While the disclosure has been described with reference to a preferred embodiment, it will be understood by those skilled in the art that various changes may be made, and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

The organic-mineral hybrid sunscreen compositions and methods of the present disclosure can comprise, consist of, or consist essentially of the essential elements and limitations of the disclosure described herein, as well as any additional or optional ingredients, components, or limitations described herein or otherwise useful. The terms "comprising," "having," and "including" are used in their open, non-limiting sense. The expression "inclusive" for a range of concentrations means that the limits of the range are included in the defined interval.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the organic-mineral hybrid sunscreen compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

As used herein, the expression "at least one" is interchangeable with the expression "one or more" and thus includes individual components as well as mixtures/combinations. The terms "a" and "the" are understood to encompass the plural as well as the singular.

The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The phrase "viscosity" refers to the thickness of a fluid or composition and is a measurement of a fluid or composition's resistance to flow. Herein, "viscosity" is synonymous to "dynamic viscosity" or "absolute viscosity", rather than "kinematic viscosity", and is measured by means of a rheometer in a method which is known to those skilled-in-the-art. Measurements of viscosity herein are reported in pascal-seconds (Pas) unless otherwise specified.

The term "INCI" is an abbreviation of International Nomenclature of Cosmetic Ingredients, which is a system of names provided by the International Nomenclature Committee of the Personal Care Products Council to describe personal care ingredients.

The term "weight ratio" or "mass ratio" as used herein, references the amount of a substance in proportion to a mixture containing said substance, and is calculated by dividing the amount of said substance by weight contained in the mixture by the weight of the mixture containing said substance. As an example, a weight ratio of 0.4 for substance A in a mixture of A, B, and C indicates that the weight of substance A divided by the total weight of substances A, B, and C is 0.4.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed:

1. An organic-mineral hybrid sunscreen composition comprising an oil-in-water emulsion, the oil-in-water emulsion comprising:
    a. an oil phase comprising:
        at least one mineral UV filter comprising zinc oxide; and
        a blend of organic UV filters comprising ethylhexyl methoxycinnamate, ethylhexyl salicylate, octocrylene, and homosalate;
    b. a water phase comprising:
        water;
        at least one water-miscible solvent; and
        at least one polymer; and
    c. at least one filler,
    wherein the organic-mineral hybrid sunscreen composition has an SPF of at least about 30 and a critical wavelength of at least 370 nm and wherein the organic-mineral hybrid sunscreen composition excludes one or more ingredients selected from the group consisting of menthyl anthranilate, parabens, and combinations thereof, and
    wherein the organic-mineral hybrid sunscreen composition is free of surfactants other than cationic surfactants comprising quaternary ammonium compounds or quaternary ammonium salts with fatty alcohols.

2. The composition according to claim 1, wherein the zinc oxide is present in an amount that is at least about 8%, the ethylhexyl methoxycinnamate is present at about 5%, the ethylhexyl salicylate is present at about 5%, the octocrylene is present at about 2%, and the homosalate is present at about 10%, all amounts by weight, based on the weight of the composition, the composition further comprising at least one oil phase solvent and at least one surfactant.

3. The composition according to claim 2, wherein the weight ratio of the UV filters to the total amount of the oil phase is about 80% (based on the total weight of the UV filters and the total weight of the oil phase), and wherein the weight ratio of the oil phase solvent to the total amount of the oil phase is equal to or less than about 5% (based on the total weight of the oil phase solvent and the total weight of the oil phase).

4. The composition according to claim 1, wherein the organic-mineral hybrid sunscreen composition excludes menthyl anthranilate.

5. The composition according to claim 1, wherein the at least one oil phase solvent comprises dimethicone.

6. The composition according to claim 1, wherein the at least one surfactant is selected from the group consisting of cationic surfactants comprising quaternary ammonium compounds.

7. The composition according to claim 1, wherein the at least one water-miscible solvent is selected from the group consisting of mono alcohols, diols, polyols, and combinations thereof.

8. The composition according to claim 1, wherein the at least one polymer is selected from the group consisting of celluloses, gums, hydrophilic colloids, and combinations thereof.

9. The composition according to claim 1, wherein the at least one filler is selected from starches.

10. The composition according to claim 1, wherein the at least one surfactant comprises cetearyl alcohol (and) behentrimonium methosulfate, the at least one water-miscible solvent comprises glycerin and propanediol, the at least one polymer comprises hydroxyethylcellulose, and the at least one filler comprises aluminum starch octenylsuccinate.

11. The composition according to claim 1, further comprising one or a combination of additives selected from the group consisting of solvents, SPF boosters, humectants, waxes, skin care actives, preservatives, pH adjusters, chelating agents, cooling agents, fragrances, dyes, pigments, and combinations thereof.

12. An organic-mineral hybrid sunscreen composition comprising an oil-in-water emulsion, the oil-in-water emulsion comprising:
 a. an oil phase comprising:
  at least one mineral UV filter comprising zinc oxide present in an amount that is at least about 8%;
  a blend of organic UV filters comprising ethylhexyl methoxycinnamate, present at about 5%, ethylhexyl salicylate, present at about 5%, octocrylene, present at about 2%, and homosalate, present at about 10%, all amounts by weight, based on the weight of the composition;
  at least one oil phase solvent comprising dimethicone; and
  at least one surfactant comprising cetearyl alcohol (and) behentrimonium methosulfate;
 b. a water phase comprising:
  water;
  at least one water-miscible solvent comprising glycerin and propanediol; and
  at least one polymer comprising hydroxyethylcellulose; and
 c. at least one filler comprising aluminum starch octenylsuccinate,
  wherein the organic-mineral hybrid sunscreen composition has an SPF of at least about 30 and a critical wavelength of at least 370 nm, and wherein the organic-mineral hybrid sunscreen composition excludes one or more ingredients selected from the group consisting of menthyl anthranilate, parabens, and combinations thereof.

13. The composition according to claim 12, wherein the weight ratio of the UV filters to the total amount of the oil phase is about 80% based on the total weight of the UV filters and the total weight of the oil phase, and wherein the weight ratio of the oil phase solvent to the total amount of the oil phase is equal to or less than about 5% based on the total weight of the oil phase solvent and the total weight of the oil phase.

14. The composition according to claim 12, further comprising one or a combination of additives selected from the group consisting of solvents, SPF boosters, humectants, waxes, skin care actives, preservatives, pH adjusters, chelating agents, cooling agents, fragrances, dyes, pigments, and combinations thereof.

15. The composition according to claim 12, wherein the organic-mineral hybrid sunscreen composition excludes menthyl anthranilate.

16. An organic-mineral hybrid sunscreen composition comprising an oil-in-water emulsion, the oil-in-water emulsion comprising:
 a. an oil phase comprising:
  at least one mineral UV filter comprising zinc oxide present in an amount that is at least about 8%;
  a blend of organic UV filters comprising ethylhexyl methoxycinnamate, present at about 5%, ethylhexyl salicylate, present at about 5%, octocrylene, present at about 2%, and homosalate, present at about 10%;
  at least one oil phase solvent comprising dimethicone, present in an amount that is equal to or less than about 2%; and
  at least one surfactant comprising cetearyl alcohol (and) behentrimonium methosulfate present at about 4.5%;
 b. a water phase comprising:
  water;
  water-miscible solvent comprising glycerin present at about 3% and propanediol present at about 3%; and
  at least one polymer comprising hydroxyethylcellulose present at about 0.5%; and
 c. at least one filler comprising aluminum starch octenylsuccinate present at about 0.5%; and
 all amounts by weight, based on the weight of the composition, wherein the organic-mineral hybrid sunscreen composition has an SPF of at least about 30 and a critical wavelength of at least 370 nm, and wherein the organic-mineral hybrid sunscreen composition excludes one or more ingredients selected from the group consisting of menthyl anthranilate, parabens, and combinations thereof.

17. The composition according to claim 16, wherein the weight ratio of the UV filters to the total amount of the oil phase is about 80%, based on the total weight of the UV filters and the total weight of the oil phase, and wherein the weight ratio of the oil phase solvent to the total amount of the oil phase is equal to or less than about 5%, based on the total weight of the oil phase solvent and the total weight of the oil phase.

18. The composition according to claim 16, further comprising one or a combination of additives selected from the group consisting of solvents, SPF boosters, humectants, waxes, skin care actives, preservatives, pH adjusters, chelating agents, cooling agents, fragrances, dyes, pigments, and combinations thereof.

19. The organic-mineral hybrid sunscreen composition according to claim 16, further comprising one or a combination of additives selected from the group consisting of solvents, SPF boosters, humectants, waxes, skin care actives, preservatives, pH adjusters, chelating agents, cooling agents, fragrances, dyes, pigments, and combinations thereof,
 wherein the organic-mineral hybrid sunscreen composition does not exhibit signs of phase separation, and/or become inhomogeneous after up to 12 weeks in an ambient temperature in the range from about 5° C. up to and including about 45° C., and maintains emulsion structural stability, with minimal color change at 60° C. for at least one week, and wherein the organic-mineral hybrid sunscreen composition excludes menthyl anthranilate.

20. A method for protecting skin from UV radiation comprising applying an effective amount of the organic-mineral hybrid sunscreen composition according to claim 1 to the skin.

* * * * *